United States Patent [19]

Palla et al.

[11] Patent Number: 4,793,851
[45] Date of Patent: Dec. 27, 1988

[54] COMPOUNDS WITH ANTIDOTAL ACTIVITY FOR THE DEFENSE OF CULTIVATIONS OF AGRARIAN INTEREST FROM THE ACTION OF NON-SELECTIVE WEED KILLERS

[75] Inventors: Ottorino Palla, Crema; Giovanni Camaggi, Lodi; Franco Gozzo, S. Donato Milanese; Ernesto Signorini, Malnate, all of Italy

[73] Assignee: Montedison S.p.A., Milan, Italy

[21] Appl. No.: 6,271

[22] Filed: Jan. 21, 1987

Related U.S. Application Data

[63] Continuation of Ser. No. 632,066, Jul. 18, 1984, abandoned.

[30] Foreign Application Priority Data

Jul. 29, 1983 [IT] Italy ................. 22343 A/83

[51] Int. Cl.$^4$ .................... C07D 513/04; A01N 43/78
[52] U.S. Cl. .......................... 71/90; 548/154
[58] Field of Search ............... 548/154; 71/90

[56] References Cited

FOREIGN PATENT DOCUMENTS 56-61390  5/1981  Japan ........................ 71/90

Primary Examiner—Robert Gerstl
Attorney, Agent, or Firm—Morgan & Finnegan

[57] ABSTRACT

This invention relates to novel compounds having antidotal activity so as to be useful in the protection of cultivations of agrarian interest from the toxic action of non-selective weed-killers. The novel compounds of this invention have the formula:

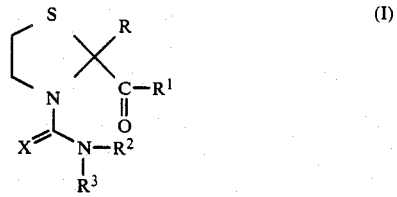

wherein R=alkyl, phenyl; $R^1$=$OR^4$=alkyl, cycloalkyl, cyclohexylmethyl, allyl, propargyl, phenyl or benzyl, optionally substituted; $R^2$=H or $R^1$ and $R^2$ together form a bond between carbonyl and the nitrogen atom which they are linked to; X=O, S; $R^3$ is the same are $R^4$, but is different from 3,5-dichlorophenyl.

6 Claims, No Drawings

COMPOUNDS WITH ANTIDOTAL ACTIVITY FOR THE DEFENSE OF CULTIVATIONS OF AGRARIAN INTEREST FROM THE ACTION OF NON-SELECTIVE WEED KILLERS

This is a continuation of co-pending application Ser. No. 632,066, filed on July 18, 1984 now abandoned.

BACKGROUND

This invention relates to compounds having the formula specified later on herein, which are useful in the protection of cultivations of agrarian interest from the toxic action of non-selective weed-killers, to the use thereof as antidotes, to compositions exerting an antidotal activity and to the preparation thereof.

The weed-killers belonging to the class of chloroacetanilides or of thiolcarbamates are very useful compounds in the fight against infesting plants of agrarian cultivations.

Many of these weed-killers, however, exert their toxic action also towards certain useful cultivations such as, for example, maize and sorghum. However, since such weed-killers are non-selective, they are not employable for the weed-killing of such cultivations.

The availability of antidotes, i.e. of compounds which protect the useful cultivations from the action of the weed-killers without reducing at the same time the weed-killing action towards the infesting plants, permits the use of these weed-killers in the protection of those useful cultivations which would be otherwise damaged.

Among the most important weed-killers which prove to be phytotoxic for certain useful cultivations there may be cited the ones belonging to the class of the chloroacetanilides which comprises for example N-methoxymethyl-2,6-diethyl-chloroacetanilide (common designation Alachlor), N-butoxymethyl-2,6-diethyl-chloroacetanilide (common designation Butachlor), N-methoxyethyl-2-methyl-6-allyl-chloroacetanilide (item M8669) and the ones belonging to the class of thiolcarbamates which comprises for example N,N-diisopropyl-S-(2,3-dichloroallyl)-thiolcarbamate (common designation Diallate); N,N-diisopropyl-S-(2,3,3-trichloroallyl)-thiolcarbamate (common desgination Triallate); N,N-diethyl-S-(4-chlorobenzyl)-thiolcarbamate (common designation Bentiocarb); N,N-dipropyl-S-ethyl-thiolcarbamate (common designation Eptam).

PRIOR ART

There are known compounds belonging to different chemical classes and which are capable of protecting useful cultivations from the toxic action of weed-killers. For example, dichloroacetamides useful as antidotes have been described in U.S. Pat. No. 4,021,224 (Stauffer) or in U.S. Pat. No. 4,228,101 (Montedison S.p.A.); 4,5-disubstituted 2-chloro-thiazoles useful as antidotes in the protection of surghum cultivations have been described in European patent application No. 27019 (Monsanto Co.).

In European patent application No. 6633 (Mitsubishi Chemical Industries) there have been described compounds endowed with a fungicidal action and having the formula:

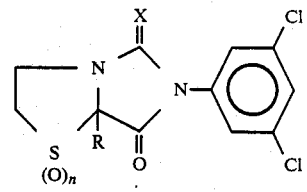

in which R=H, alkyl $C_1$-$C_4$; X=O, S; n=)0, 1, 2.

Intermediates for the synthesis of these compounds are the compounds of formula:

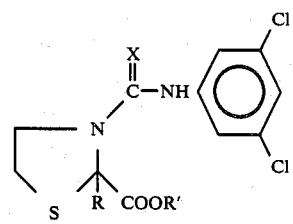

in which R and X have the meanings indicated hereinabove and R'=H, an alkyl $C_1$-$C_5$.

OBJECTS OF THE INVENTION

An object of the present invention is to provide a method of reducing the damages caused to useful cultivations by non-selective weed-killers belonging for example to the class of chloroacetanilides of of thiolcarbamates, such method consisting in treating the seeds, the plates or the soil in which they grow with an effective amount of an antidote of formula I either as such or as a suitable composition.

Another object of the invention is to provide compositions containing antidote compound as an active ingredient, besides inert carriers and optionally other additives, useful to treat the seeds of useful plants, the plants themselves or the soil in which they grow.

A further object of the invention is useful plants' seeds treated with an effective amount of an antidote compound of the present invention.

GENERAL DESCRIPTION OF THE INVENTION

It has been found that the objects of this invention may be realized by using as antidotes a compound having the formula:

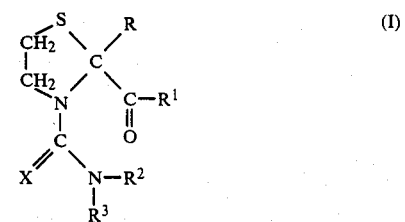

in which:

R is an alkyl $C_1$-$C_4$ or a phenyl;

$R^1$ is a group $OR^4$ in which $R^4$ is an alkyl $C_1$-$C_8$; a cycloalkyl $C_5$-$C_6$ a cyclohexylmethyl; an allyl; a propargyl; a phenyl or a benzyl, the last two being in their turn optionally substituted by from one to three groups selected from atoms of halogen, alkyl-$C_1$-$C_4$, alkoxyl $C_1$-$C_4$, nitro- and trifluoromethyl;

$R^2$ is a hydrogen atom;

or R' and R² together form a bond between the carboyl to which R¹ is linked and the nitrogen atom to which R² is linked;

X is an oxygen atom or an atom of divalent sulphur;

R³ has the same meanings as R⁴ but is different from 3,5-dichlorophenyl.

The toxic action of non-selective weed-killers belonging for example to the class of chloroacetanilides and of thiolcarbamates towards useful cultivations can be considerably reduced or eliminated, without simultaneously losing the weed-killing action towards infesting plants, if the compounds of formula I are employed as antidotes.

Specific examples of compounds of formula I are those having a monocyclic structure

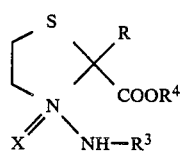

(I-A)

or a bicyclic structure

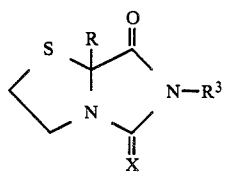

(I-B)

For nomenclature conventions, the compounds of formula I-A are designated as 2-substituted esters of N-carbamoyl (or thiocarbamoyl)-thiazolidin-2-carboxylic acid and the compounds of formula I-B are designated as derivatives of perhydro-imidazo[5,1-b]-thiazol-5,7-dione or 5-thione-7-one in which substituent R is in position 7a and substituent R³ is in position 6.

Among the compounds of formula I-A there may be cited the ones having formula:

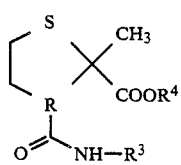

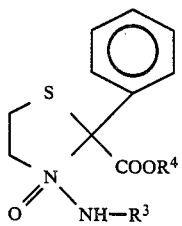

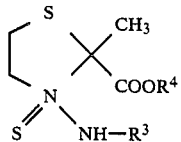

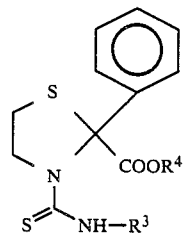

in which R³ and R⁴ have the meanings specified for formula I.

Analogously, among the compounds of formula I-B there may be cited the ones having formula

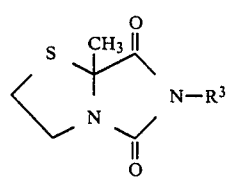

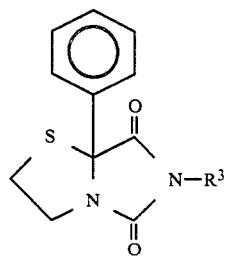

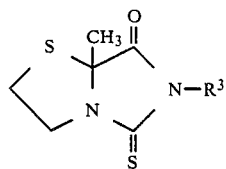

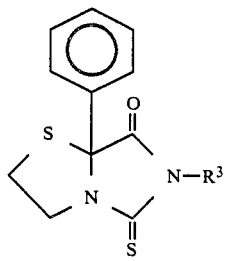

in which R³ has the meanings indicated for formula I.

The compounds of formula I are prepared according to one of the procedures described hereinbelow (symbols R, R¹, R², R³, R⁴ and X have the same meanings as are indicated for formula I).

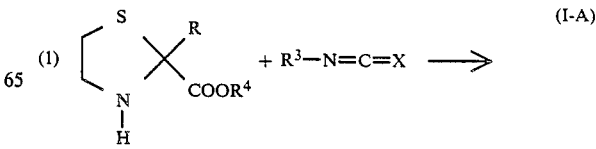

(1)                                                                              (I-A)

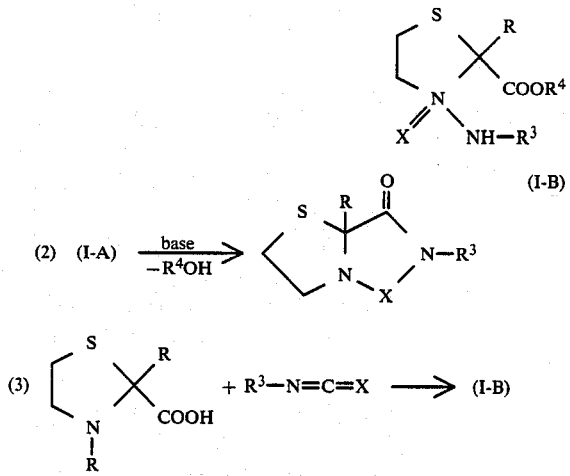

The compounds of formula I-A are obtained by reacting an ester of the thiazolidin-2-carboxylic acid, either 2-alkyl or 2-phenyl-substituted, with the proper isocyanate or isothiocyanate according to reaction 1.

When starting from a free thiazolidin-2-carboxylic acid instead of from the ester, the compounds of formula I-B according to reaction 3 are obtained.

The compounds of formula I-B are also obtained by operating an intramolecular condensation on the compounds of formula I-A by treatment with a base according to reaction 2.

Reaction 1 is conducted in an inert solvent, such as for example, a chlorinated hydrocarbon, and at a temperature ranging from the room temperature and the reflux temperature of the reaction mixture.

Reaction 2 is conducted in the presence of a base in an inert solvent, for example, in a system consisting of sodium ethylate in ethanol, and at the reflux temperature of the reaction mixture.

Reaction 3 is carried out by suspending the thiazolidin-carboxylic acid in an aprotic polar solvent, for example, dimethylformamide, and by adding to the suspension a solution of the isocyanate (or isothiocyanate) in an inert solvent, for example, a chlorinated hydrocarbon such as chloroform; the reaction occurs at temperatures between 20° and 60° C.

The starting thiazolidin-carboxylic acids and esters are known compounds or compounds easily preparable according to known methods, for example, by reaction between cisteamine and an alpha-keto-acid (see for example European patent application No. 6633 cited hereinbefore).

The starting isocyanates or isothiocyanates are too known compounds or compounds easily preparable according to conventional methods.

As already mentioned herein, the antidotes of formula I can be applicated to the useful cultivations according to various modalities.

For example, they can be utilized for a preventive seed dressing so that the plant which will develop from such seed may be protected from the toxic action of the non-selective weed-killers.

As an alternative, the compounds of formula I can be employed for the treatment just of the plant or of the earth in which it grows. In this case, the antidotes can be distributed either alone or in combination with the non-selective weed-killer.

The different types of application require different conditions which will affect the practical aspects of the treatment, such as amount of antidote, time of treatment and type of composition.

Other factors affecting the practical aspects of the treatment are the type of cultivation to be protected, the non-selective weed-killer employed, climatic and environmental conditions.

When the antidote is applicated in a preventive seed dressing, it can be utilized either as such or preferably as a suitable composition.

The compositions for the seed dressing may be in the form of powders, wettable powders or emulsifiable concentrates, and in general they consist of the active compounds in amounts of from 0.5 to 95% by weight and of the usual inert carriers which, independently of the type of composition, can be solid such as talc, silica, diatomite, bentonite, calcium carbonate and mixtures thereof, or liquid such as water, alkyl-aromatic hydrocarbons, acetone, cyclohexanone and mixtures thereof.

Also, proper additives such as surfactants, dispersants and mixtures thereof may be present in the compositions.

A specific example of composition in powder for the seed-dressing is the following:

| | |
|---|---|
| compounds of formula I | 25–75% by weight |
| mixture of a wetting agent, a dispersant and an adhesion promoting agent | 1–5% by weight |
| solid inert carrier | 20–74% by weight |

Examples of useful wetting agents are polyoxyethylated nonyl-phenols, sodium alkylnaphthalensulphonates, sodium alkylsulphosuccinates; examples of dispersants are sodium lignosulphonates, calcium lignosulphonates or aluminium lignosulphonates, sodium alkylnaphthalensulphonates condensed with formaldehyde, maleic anhydride-diisobutylene copolymers; examples of adhesivants are glycols, glycerine, polyglycols, arabic gum, starch, sodium polymethacrylate with different molecular weights.

All these additives are well known in the formulative field and are commercially available also in already prepared mixtures.

The abovesaid compositions are prepared by mixing the ingredients and homogenizing same by means of grinding till obtaining the desired granulometry.

Such compositions are utilizable as such for dry dressing the seeds, or diluted with some water for the wet dressing.

As indicated hereinbefore, the antidote amount to be distributed onto the seeds varies as a function of different factors; still, it is generally sufficient to use product amounts ranging from 0.1 to 100 g/kg of seeds.

The treatments directly accomplished on the plant or in the medium in which the plant grows require, of course, the use of the antidote in the form of a suitable composition according to the usual practice for the type of application.

In the applications in which the antidote is distributed onto the vegetation or in the soil along with the non-selective weed-killer in an only formulation, the type of formulation and the content vary both in relation to the factors cited hereinabove and in relation to the type of weed-killer employed and to the characteristics thereof.

The antidote amount to be employed generally ranges from 0.1 to 10 kg/ha and the ratio between antidote and weed-killer in the compositions may range from 1:5 to 5:1 by weight.

However, in relation to certain combination between cultivation to be protected, type of non-selective weed-killer and relative effectiveness of the compound of formula I taken into consideration, the antidote amount for the treatment in the soil or on the vegetation may be also of only 10 g/ha and the ratio between antidote and weed-killer in the composition can be reduced even to values near 1:1000 by weight.

SPECIFIC DESCRIPTION OF THE INVENTION

The following examples are given with a view to better illustrating the present invention.

EXAMPLE I

Preparation of compound 7a-phenyl-6-methyl-perhydroimidazo-[5,1-b]-thiazol-5,7-dione [Compound No. 1]

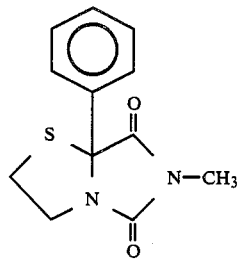

To a suspension of 1 g (0.005 moles) of 2-phenyl-thiazolidin-2-carboxylic acid (prepared from cisteamine and phenylglyoxylic acid) in 20 ml of anhydrous dimethylformamide (DMF) there was added a solution of 2.3 g (0.005 moles) of methylisocyanate in 10 ml of $CHCl_3$.

The reaction mixture was heated to 35° C. for 1.5 hours. After cooling to room temperature, 40 ml of hydrochloric acid at 8% and 100 ml of $CHCl_3$ were added to the mixture.

The organic phase was separated, washed with water ($3 \times 100$ ml) and anhydrified on anhydrous $Na_2SO_4$.

By removal of the solvent under reduced pressure, the desired product was obtained, which was crystallized from hexane and ethyl acetate, thus obtaining 0.7 g of solid product with a melting point of 100°–102° C.

IR: significant bands at 1770 and 1705 cm$^{-1}$ ($\nu C=O$).
$^1$H-NMR (CDCl$_3$, TMS). $\delta$(ppm) 3.05, (s, 3H, N—CH$_3$), 2.90–3.50, (m, 3H), 4.45–4.75, (m, 1H), 7.2–7.7, (m, 5H, aromatic protons), s=singlet, m-multiplet).

EXAMPLE 2

Preparation of compound 6,7a-dimethyl-perhydro-imidazo-[5,1-b]-thiazol-5,7-dione [compound No. 2]

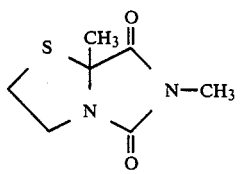

By operating in like manner as is described in Example 1 and by starting from 2-methyl-thiazolidin-2-carboxylic acid and methyl isocyanate, the desired product was obtained as a white solid having a melting point of 67°–68° C.

IR: significant bands at 1775 and 1720 cm$^{-1}$ ($\nu C=O$).
$^1$H-NMR (CDCl$_3$, TMS). $\delta$(ppm); 1.78, (s, 3H, C—CH$_3$), 3.03, (s, 3H, C—CH$_3$), 2.85–3.45, (m, 3H), 4.30–4.65, (m, 1H), (s=singlet, m=multiplet).

EXAMPLE 3

Preparation of compound 6-ethyl-7a-phenyl-perhydroimidazo-[5,1-b]-thiazol-5,7-dions [compound No. 3]

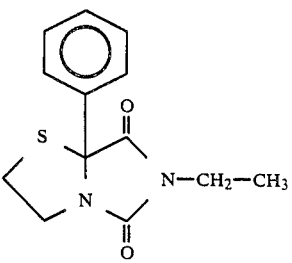

By operating in like manner as is described in Example 1 starting from 2-phenyl-thiazolidin-2-carboxylic acid and from ethyl-isocyanate, the desired compound was obtained as a white solid having a melting point of 83°–84° C.

IR: significant bands at 1770 and 1700 cm$^{-1}$ ($\nu C=O$).

EXAMPLE 4

Preparation of compound ethyl ester of N-phenylcarbamoyl-2-methyl-thiazolidin-2-carboxylic acid [Compound No. 4]

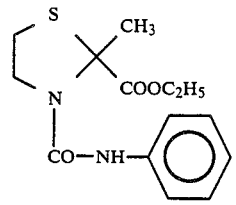

To a solution of 1.75 g (0.01 moles) of ethyl ester of 2-methyl-thiazolidin-2-carboxylic acid in 20 ml of chloroform (CHCl$_3$) there was added a solution of 1.2 g (0.01 moles) of phenyl-isocyanate in 20 ml of CHCl$_3$.

The mixture was then heated to reflux temperature for 6 hours.

After cooling to room temperature, the solution was washed with water and anhydrified on anhydrous Na$_2$SO$_4$.

After removal of the solvent by evaporation under reduced pressured, there were obtained 3.5 g of a rough product, which was distempered in a hexane-ethyl acetate (3:1) mixture, thus obtaining 2.5 g of the desired pure product as a crystalline solid having a melting point of 129°–130° C.

IR: significant bands at 1628 cm$^{-1}$ ($\nu$CO—N), 1722 cm$^{-1}$ ($\nu$COO) and 3280 cm$^{-1}$ ($\nu$NH).

EXAMPLE 5

Preparation of compound 6-phenyl-7a-methyl-perhydro-imidazo-[5,1-b]-thiazol-5,7-dione [Compound No. 5]

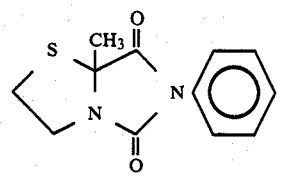

A solution obtained by dissolving 0.2 g (0.005 moles) of metal sodium in 20 ml of anhydrous ethanol was added to a suspension of 1.5 g (0.005 moles) of compound No. 4 (prepared as described in Example 4) in 20 ml of anhydrous ethanol.

On conclusion of the addition, the reaction mixture was heated at reflux for 6 hours.

It was then allowed to stand overnight at room temperature, whereafter the solvent was removed by evaporation under reduced pressure and the residue was diluted again with 100 ml of ethyl acetate.

The resulting solution was washed with water (3 times with 30 ml each) and anhydrified on anhydrous $Na_2SO_4$. The solvent was removed by evaporation under reduced pressure, so obtaining 0.7 g of the desired product as a while solid having a melting point of 145°–147° C.

IR: significant bands at 1770–1710 $cm^{-1}$ ($\nu C=O$).

EXAMPLE 6

Determination of the antidotal activity on wheat by seed dressing.

There was prepared a composition for the seed dressing

| consisting of: | |
|---|---|
| compound of formula I | 25% by weight |
| nonylphenol polyoxyethylate | 0.5% by weight |
| sodium lignosulphonate | 0.5% by weight |
| glycerine | 0.1% by weight |
| kieselguhr (diatomite) | 73.9% by weight |

The compounds were mixed and homogenized by means of grinding till obtaining a fine powder.

Wheat seeds were treated with the above-described composition at a dose of 10 g of active substance (compound of formula I) per kg of seeds.

The day after, the dressed seeds were sowed into pots containing a sandy earth.

The pots were then sprayed with a solution, in dimethylsulphoxide, of weed-killer Alachlor at a concentration corresponding to a practical dose of 0.75 and 1.5 kg/ha of weed-killer.

As a check there were used a set of pots containing seeds dressed neither with the antidote nor with the weed-killer, and a set of pots containing seeds dressed with the weed-killer but not with the antidote.

All the pots were then kept in a conditioned environment at 15°–24° C., relative humidity=70%, photoperiod=12 hours.

The pots were regularly watered to secure a normal growth of the plants.

Three weeks after sowing, the antidotal activity was determined by comparing the growth of the plants treated both with the antidote (seed dressing) and with the weed-killer with the growth of the non-treated plants or of those treated only with the weed-killer.

The results were expressed on the basis of the vegetative state of the plant by means of a scale of values from 4 (complete stop of the growth or death of the plant) to 0 (sound plant, growth like that of the check grown in the absence of weed-killer and of antidote). By consequence, a numerical evaluation like that of the plants treated with the weed-killer only is indicative of the absence of any antidotal effect, while an evaluation equal to zero indicates a full protection of the plant from the toxic action exerted by the weed-killer; the intermediate values indicate a partial antidotal effect, increasing towards the lowest values.

Compound No. 1 (see example 1) showed a complete antidotal activity on wheat (evaluation=0) against the damages caused by Alachlor at a dose of 0.75 and of 1.5 kg/ha.

At the same doses, the weed-killer Alachlor caused a complete stop of the growth (evaluation=4) of the check in the absence of the antidote.

What is claimed is:

1. Compounds of formula

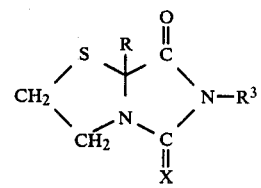

wherein X is oxygen, $R_3$ is methyl or ethyl and R is phenyl or $C_1$–$C_4$ alkyl.

2. The compound according to claim 1, 6,7a-dimethylperhydro-imidazo-[5,1-b]-thiazol-5,7-dione.

3. The compound according to claim 1, 7a-phenyl-6-methyl-perhydro-imidazo-[5,1-b]-thiazol-5,7-dione.

4. The compound according to claim 1, 6-ethyl-7a-phenyl-perhydro-imidazo-[5,1-b]-thiazol-5,7-dione.

5. A method of reducing the damages caused to useful cultivations by weed killers belonging to the class of the chloroacetanilides or of the thiolcarbamates, consisting in treating the seeds, the plants or the soil in which they grow with an effective amount of a compound endowed with an antidotal activity, said compound of the formula

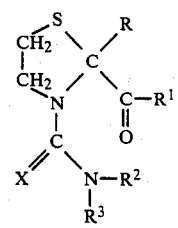

in which

R is an alkyl $C_1$–$C_4$ or a phenyl;

$R^1$ is a group $OR^4$ in which $R^4$ is an alkyl $C_1$–$C_8$; a cycloalkyl $C_5$–$C_6$; a cyclohexylmethyl; an allyl; a propargyl; a phenyl or benzyl, the last two being in turn optionally substituted by one to three groups selected from atoms of halgen, alkyl $C_1$–$C_4$, alkoxyl $C_1$–$C_4$, nitro and trifluoromethyl;

$R^2$ is a hydrogen atom;

or $R^1$ and $R^2$ together form a bond between the carbonyl which $R^1$ is bound to and the nitrogen atom which $R^2$ is bound to;

X is an atom of oxygen or of divalent sulphur;

$R^3$ is the same as $R^4$ but is different from 3,5-dichlorophenyl.

6. The method according to claim 5, characterized in that the non-selective weed-killer is the weed-killer known as Alachlor or the weed-killer known as Eptam.

* * * * *

UNITED STATES PATENT AND TRADEMARK OFFICE
CERTIFICATE OF CORRECTION

PATENT NO. : 4,793,851

DATED : December 27, 1988

INVENTOR(S) : Ottorino Palla; Giovanni Camaggi; Franco Gozzo and Ernesto Signorini It is certified that error appears in the above-identified patent and that said Letters Patent is hereby corrected as shown below:

In the Abstract:
Second line from bottom, "are", second occurrence, should read -- is --.

In the Specification:
Column 1, line 61, "surghum" should read --sorghum--.
Column 2, line 31, after "chloroacetanilides" delete "of" first occurrence.
Column 9, line 30, "while" should read --white--.

In the Claims:
Claim 5, line 68, "halgen" should read --halogen--.

Signed and Sealed this

Twelfth Day of September, 1989

Attest:

DONALD J. QUIGG

Attesting Officer

Commissioner of Patents and Trademarks